United States Patent
Ruchti et al.

(10) Patent No.: US 6,501,982 B1
(45) Date of Patent: Dec. 31, 2002

(54) SYSTEM FOR THE NONINVASIVE ESTIMATION OF RELATIVE AGE

(75) Inventors: Timothy L. Ruchti, Gilbert, AZ (US); Suresh Thennadil, Tempe, AZ (US); Stephen F. Malin, Glendale, CA (US); Jessica Rennert, Scottsdale, AZ (US)

(73) Assignee: Sensys Medical, Inc., Chandler, AZ (US)

(*) Notice: Subject to any disclaimer, the term of this patent is extended or adjusted under 35 U.S.C. 154(b) by 0 days.

(21) Appl. No.: 09/487,236

(22) Filed: Jan. 19, 2000

Related U.S. Application Data

(63) Continuation-in-part of application No. 09/359,191, filed on Jul. 22, 1999, now Pat. No. 6,280,381.
(60) Provisional application No. 60/116,883, filed on Jan. 22, 1999.

(51) Int. Cl.[7] ................................. A61B 6/00
(52) U.S. Cl. ................. 600/473; 600/322; 600/310; 600/475
(58) Field of Search ................. 600/310, 473, 600/476, 477; 250/338.1, 340, 341.5, 341.8

(56) References Cited

U.S. PATENT DOCUMENTS

| | | | | |
|---|---|---|---|---|
| 4,894,547 A | * | 1/1990 | Leffell et al. | 250/461.2 |
| 5,701,902 A | * | 12/1997 | Vari et al. | 128/664 |
| 5,879,294 A | * | 3/1999 | Anderson et al. | 600/310 |
| 5,931,779 A | | 8/1999 | Arakaki et al. | 600/310 |
| 6,006,119 A | * | 12/1999 | Soller et al. | 600/322 |
| 6,061,582 A | * | 5/2000 | Small et al. | 600/316 |

FOREIGN PATENT DOCUMENTS

| WO | 97/36540 | 10/1997 |
|---|---|---|

OTHER PUBLICATIONS

Tormod Naes and Kjell Ivar Hildrum; *Comparison of Multivariate Calibration and Discriminant Analysis in Evaluating NIR Spectroscopy for Determination of Meat Tenderness*; 1997; Applied Spectroscopy; vol. 51, No. 3.

A. Brooks; N. Afanasyeva; V. makhine; R.F. Bruch; S. F. Kolyakov; S. Artjushenko; and L. N. Butvina; *New Method for Investigations of Normal Human Skin Surfaces in vivo Using Fiber–optic Evanescent Wave Fourier Transform Infrared Spectroscopy (FEW–FTIR)*; Surface and Interface Analysis, Heyden and Son, London GB, vol. 27, No. 4; Apr. 1999.

Andrew, W., R.H. Behnke and T. Sato. "Changes with advancing age in the cell population of human dermis," *Gerontologia*, vol. 10, pp. 1–19, 1964/65.

(List continued on next page.)

*Primary Examiner*—Marvin M. Lateef
*Assistant Examiner*—Devaang Shah
(74) *Attorney, Agent, or Firm*—Michael A. Glenn; Christopher Peil

(57) ABSTRACT

Noninvasive instrumentation and procedures have been developed for estimating the apparent age of human and animal subjects based on the irradiation of skin tissue with near-infrared light. The method of age estimation provides additional information about primary sources of systematic tissue variability due to chronological factors and environmental exposure. Therefore, categorization of subjects on the basis of the estimated apparent age is suitable for further spectral analysis and the measurement of biological and chemical compounds, such as blood analytes. Furthermore, age determination of subjects has particular benefit in assessment of therapies used to reduce the effects of ageing in tissue and measurement of tissue damage.

66 Claims, 10 Drawing Sheets

OTHER PUBLICATIONS

Montagna, W. and K.C. Carlisle. "Structural xhanges in aging human skin," *The Journal of Investigative Dermatology*, vol. 73, pp. 47–53, 1979.

Brocklehurst, J.C. Textbook of Geriatric Medicine and Gerontology, Churchill Livingstone, Edinburgh and London, pp. 593–623, 1973.

Khalil OS. Spectroscopic and clinical aspects of non–invasive glucose measurements. Clin Chem 1999; 45: 165–77.

Roe, JN and BR Smoller. "Bloodless Glucose Measurements," Critical Reviews in Therapeutic Drug Carrier Systems, vol. 15, No. 3, pp. 199–241, 1998.

Oikarinen, A., "Aging of the skin connective tissue: how to measure the biochemical and mechanical properties of aging dermis," *Photodermatology Photoimmunology& Photomedicine* 1994: 10:47–52.

Fenske, N.A. and C. Lober, "Structural and functional changes of normal aging skin," *J Am Acad Dermatol* 1996: 15: 571–583.

Gniadecka, M. and G.B.E. Jemec, "Quantitative evaluation of chronological aging and photoaging *in vivo*: studies on skin echogenicity and thickness," *Br J Dermatol* 1998: 139: 815–821.

Stern, R.S., "The Measure of Youth," *Architecture Dermatol* 1992: 128: 390–393.

Rigal, J., C. Escoffier, B. Querleux, B. Faivre, P. Agache, J. Leveque, "Assessment of Aging of the Human Skin by In Vivo Ultrasonic Imaging," *Society for Investigative Dermatology* 1989:93: 621–625.

Quan, M.B., C. Edwards and R. Marks, "Non–invasive *In Vivo* Techniques to Differentiate Photodamage and Aging in Human Skin," *Acta Derm Venereol* 1997: 77:416–419.

Martens, H. and T. Naes. Multivariate Calibration. New York: John Wiley and Sons, 1989: 419 pp.

Geladi, P. and D. McDougall and H. Martens. "Linearization and Scatter–Correction for Near–Infrared Reflectance Spectra of Meat," *Applied Spectroscopy*, 1985: 39: 491–500.

Savitzky, A. and M.J.E. Golay. "Smoothing and Differentiation of Data by Simplified Least Squares Procedures," Anal. Chem., vol. 36, No. 8, pp. 1627–1639, 1964.

Geladi, P. and B.R. Kowalski, "Partial least–squares regression: a tutorial." *Analytica Chimica Acta*, 185, pp. 1–17, 1986.

Duda, R.O. and P.E. Hart, *Pattern Classification and Scene Analysis*, John Wiley and Sons, New York, 1973.

Wold, S. and M. Sjostrom. "SIMCA: A method for analyzing chemical data in terms of similarity and analogy," *Chemometrics: Theory and Application*, ed. B.R. Kowalski, ACS Symposium Series, 52, 1977.

Bezdek, J.C. and S.K. Pal, eds. Fuzzy Models for Pattern Recognition. IEEE Press, Piscataway, NJ, 1992.

Keller, J., M. Gray and J. Givens. "A Fuzzy K nearest Neighbor Algorithm," IEEE Transactions on Systems, Man, and Cybernetics, vol. SMC–15, No. 4, pp. 580–585, Jul./Aug., 1985.

Pao, Y.H. *Adaptive Pattern Recognition and Neural Networks*. Addison–Wesley Publishing Company, Inc., Reading, MA, 1989.

Chen, C.H., ed., Fuzzy Logic and Neural Network Handbook, Piscataway, NJ: IEEE Press, 1996.

Zadeh, L.A. "Fuzzy Sets," Inform. Control, vol. 8, pp. 338–353, 1965.

* cited by examiner

SYSTEM FOR THE NONINVASIVE ESTIMATION OF RELATIVE AGE

This application is a continuation-in-part of S. Malin, T. Ruchti, An Intelligent System for Noninvasive Blood Analyte Prediction, U.S. patent application Ser. No. 09/359,191, filed Jul. 22, 1999, which claims priority from Provisional Patent Application No. 60/116,883, filed Jan. 22, 1999.

BACKGROUND OF THE INVENTION

1. Technical Field

The invention relates to the estimation of the apparent age of in vivo skin tissue. More particularly, the invention relates to the instrumentation and method by which the age and general tissue parameters of subjects can be estimated and classified through noninvasive tissue measurements.

2. Description of the Prior Art

Near-infrared (NIR) tissue spectroscopy is a promising noninvasive technology that bases measurements on the irradiation of a tissue site with NIR energy in the 700–2500 nanometer wavelength range. The energy is focused onto an area of the skin and propagates according to the scattering and absorption properties of the skin tissue. Thus, the reflected or transmitted energy that escapes and is detected provides information about the tissue volume encountered. Specifically, the attenuation of the light energy at each wavelength is a function of the structural properties and chemical composition of the tissue. Tissue layers, each containing a unique heterogeneous particulate distribution, affect light absorbance through scattering. Chemical components such as water, protein, fat and blood analytes absorb light proportionally to their concentration through unique absorption profiles or signatures. The measurement of tissue properties, characteristics or composition is based on detecting the magnitude of light attenuation resulting from its respective scattering and/or absorption properties. The chronological age and type and duration of environmental exposure of skin tissue have a pronounced effect on the properties of tissue and is a primary factor in tissue variability between individuals. See, for example, W. Andrew, R. Behnke, T. Sato. Changes with advancing age in, the cell population of human dermis, Gerontologia, vol. 10, pp. 1–19, (1964/65); W. Montagna, and K. Carlisle. Structural changes in ageing human skin, The Journal of Investigative Dermatology, vol. 73, pp. 47–53, 1979. J. Brocklehurst, *Textbook of Geriatric Medicine and Gerontology,* Churchill Livingstone, Edinburgh and London, pp.593–623 (1973).

Therefore, NIR tissue spectroscopy can be used to detect, quantify, and monitor age related effects in tissue through a noninvasive measurement process. Moreover, NIR tissue spectroscopy has particular benefit in several areas including estimation of blood analytes, assessment and monitoring of therapies. used to reduce the effects of ageing in tissue and diagnosis and quantification of tissue damage.

Blood Analyte Prediction

While noninvasive prediction of blood analytes, such as blood glucose concentration, has been pursued through NIR spectroscopy, the reported success and product viability has been limited by the lack of a system for compensating for structural variations between individuals that produce dramatic changes in the optical properties of the tissue sample See, for example, O. Khalil. Spectroscopic and clinical aspects of non-invasive glucose measurements, Clin Chem (1999) vol. 45, pp.165–77, and J. Roe and B. Smoller, Bloodless Glucose Measurements, Critical Reviews in Therapeutic Drug Carrier Systems, vol. 15, no. 3, pp. 199–241 (1998).

These differences are largely anatomical and provide distinct systematic spectral absorbance features or patterns that can be related directly to specific characteristics such as dermal thickness, protein levels, structure of collagen bundles, dermal thinning, hydration, flattening of the epidermal-dermal junction and thickness of the subcutaneous layer. While the absorbance features are repeatable by subject over short periods of time, over a population of subjects they produce confounding nonlinear spectral variation. In addition, the changes of skin tissue of an individual as the result of chronological ageing and/or environmental exposure lead to profound differences in the volume of tissue sampled by the NIR measurement device. Therefore, differences between subjects and within subjects over time are a significant obstacle to the noninvasive measurement of blood analytes through NIR spectral absorbance.

Previously, in the parent application to the current application, S. Malin and T. Ruchti, An Intelligent System For Noninvasive Blood Analyte Prediction. U.S. patent application Ser. No. 09/359,191, filed Jul. 22, 1999 an apparatus and procedure for substantially reducing this problem by classifying subjects according to major skin tissue characteristics prior to blood analyte prediction was disclosed. The selected characteristics are representative of the properties of the actual tissue volume irradiated and the amount of the target analyte that is sampled. By grouping individuals according to the similarity of spectral characteristics representing the tissue structure, the nonlinear variation described above is reduced and estimation of blood analytes becomes more accurate. Specifically, classification of NIR spectral data according to the apparent age or condition of the tissue will improve the accuracy and robustness of models for estimating tissue/blood parameters, such as blood analytes, through the significant reduction of sample variability without the addition of other measurement devices (see S. Malin and T. Ruchti, An Intelligent System For Noninvasive Blood Analyte Prediction, U.S. patent application Ser. No. 09/359,191, filed Jul. 22, 1999).

Apparent Ageing of Skin Tissue

The effects of ageing on skin tissue include two separate phenomena: chronological and photo ageing. Chronological ageing is typified by natural changes in the skin over time, such as dermal thinning, changes in level of hydration, flattening of the epidermal-dermal junction and reduced sebum/sweat production.

For example, see A. Oikarinen, Ageing of the skin connective tissue: how to measure the biochemical. and mechanical properties. of ageing dermis, Photodermatology Photoimmunology & Photomedicine (1994) vol. 10, pp. 47–52; N. Fenske, and C. Lober, Structural and functional changes of normal ageing skin, J Am Acad Dermatol (1996) vol. 15, pp. 571–583; M. Gniadecka, and G. Jemec, Quantitative evaluation of chronological ageing and photo ageing in vivo: studies on skin echogenicity and thickness, Br J Dermatol (1998) vol. 139, pp. 815–821.

Photo ageing is an alteration or damaging of skin as a result of sun exposure, manifested by dryness, solar elastosis, irregular pigmentation and fine wrinkling, and is the cause of premature ageing of skin. See, for example R. Stern, The Measure of Youth, Arch Dermatol (1992) vol. 128, pp. 390–393.

Ultrasound has been used to reveal that changes in the upper dermis are related to photo ageing and changes in the lower dermis are related to chronological ageing. See A. Oikarinen, Ageing of the skin connective tissue: how to measure the biochemical and mechanical properties of ageing dermis, Photodermatology Photoimmunology & Photomedicine (1994) vol. 10, pp. 47–52. The upper dermis becomes thicker (solar elastosis) with increased sun exposure and the lower dermis degrades with chronological age. See J. Rigal, C. Escoffier, B. Querleux, B. Faivre, P. Agache, J. Leveque, Assessment of Ageing of the Human Skin by In Vivo Ultrasonic Imaging, Society for Investigative Dermatology (1989) vol. 93, pp. 621–625.

As a result of societal pressure for tanned young skin, pharmaceutical and cosmetic companies have been developing and marketing products that claim to repair the effects of photo-damage to skin and restore skin to its youthful condition. The ability to quantitatively measure the apparent age or condition of tissue is useful in determining the effectiveness of topical drugs used to reverse damage due to photo ageing . See R. Stern, The Measure of Youth, Arch Dermatol, (1992), vol. 128, pp. 390–393. An in vivo, quantitative technique would be of great benefit in assessing the effectiveness of treatments for photo-damaged tissue. See M. Quan, C. Edwards, and R. Marks, Non-invasive In Vivo Techniques to Differentiate Photodamage and Ageing in Hu7man Skin, Acta Derm Venereol, vol. 77, pp. 416–419 (1997).

However, no technique has been reported for quantitatively determining apparent age on the basis of a noninvasive measurement. Existing methods for age determination generally rely on invasive procedures or subjective evaluation. The amount of photo-damage and the effects of age-reversing drugs are typically determined by visual inspection of the skin by a trained individual and subsequent assignment of a grade representing the degree of damage. Several groups have proposed methods using standardized photographs representation the different degrees of sun damage in an attempt to standardize the age ratings. These methods have been found to be subjective and not repeatable. Furthermore, these qualitative methods only provide a surface measurement of the effectiveness of the product being tested and do not provide any information. about true structural or chemical changes in the tissue. See R. Stern, The measure of Youth, Arch Dermatol, vol. 128, pp. 390–393 (1992).

SUMMARY OF THE INVENTION

The present invention provides a method and apparatus for non-invasively determining the apparent age tissue, in vivo. A spectroscopic apparatus in conjunction with an optical interface is used to measure tissue properties and characteristics that are manifested spectrally and that vary systematically according to the subject's age and environmental exposure. A novel method is disclosed that uses in vivo, non-invasive NIR measurements to estimate the apparent age of the skin and/or classify the skin according to predefined age group categories.

The procedure for age estimation employs a calibration model that is empirically derived from a set of exemplary samples consisting of NIR tissue measurements and the actual chronological age of a population of subjects. The model is a set of parameters and computer generated code that is implemented to estimate the subject's age. The estimation consists of an actual age determination in years and one or more relative property magnitudes that reveal information regarding the tissue properties of the sampled tissue volume.

The apparent age estimate provides a reliable and repeatable quantitative measure of the condition of the skin with respect to the combined effects of chronological ageing and photo ageing. In addition, magnitude of the two types of ageing is deduced from NIR measurements by targeting specific tissue volumes and/or decomposing the measurements through multivariate factor analysis to reveal underlying variation correlated to specific ageing related tissue parameters such as dermal thickness and hydration. The resulting age estimation and/or classification is also suitable for categorization of spectral data prior to blood analyte prediction.

DETAILED DESCRIPTION

The current invention provides an apparatus for measuring the infrared absorption by tissue irradiated with near-infrared energy, a procedure for estimating the subject's age and a procedure for classifying the subject into age related categories for further spectral analysis and blood analyte prediction.

Apparatus

The apparatus includes an energy source, a sensor element, an interface 15 to the subject 10, a wavelength selection device and an analyzer. The energy source generates and transmits near-infrared energy in the wavelength range 700–2500 nanometers and consists of a device such as an LED array. or a quartz halogen lamp. The method of wavelength separation includes a monochromator, an interferometer or successive illumination through the elements of an LED array. The optical interface 15 includes a means for transmitting energy 13 from the source to the target skin tissue measurement site; for example, a light pipe, a fiber-optic probe, a lens system or a light directing mirror system, and a means for collecting energy 14 from the target site. Energy is collected from the surrounding tissue areas in reflectance mode at an optimally determined distance(s)

through the use of starring detectors or fiber-optic probes. Alternately, energy is collected in transmission mode through a skin flap, ear lobe, finger or other extremity. The sensing elements are detectors that are responsive to the targeted wavelengths the collected light is converted to a voltage and sampled through an analog-to-digital converter for analysis on a microprocessor-based system.

Figure 1:
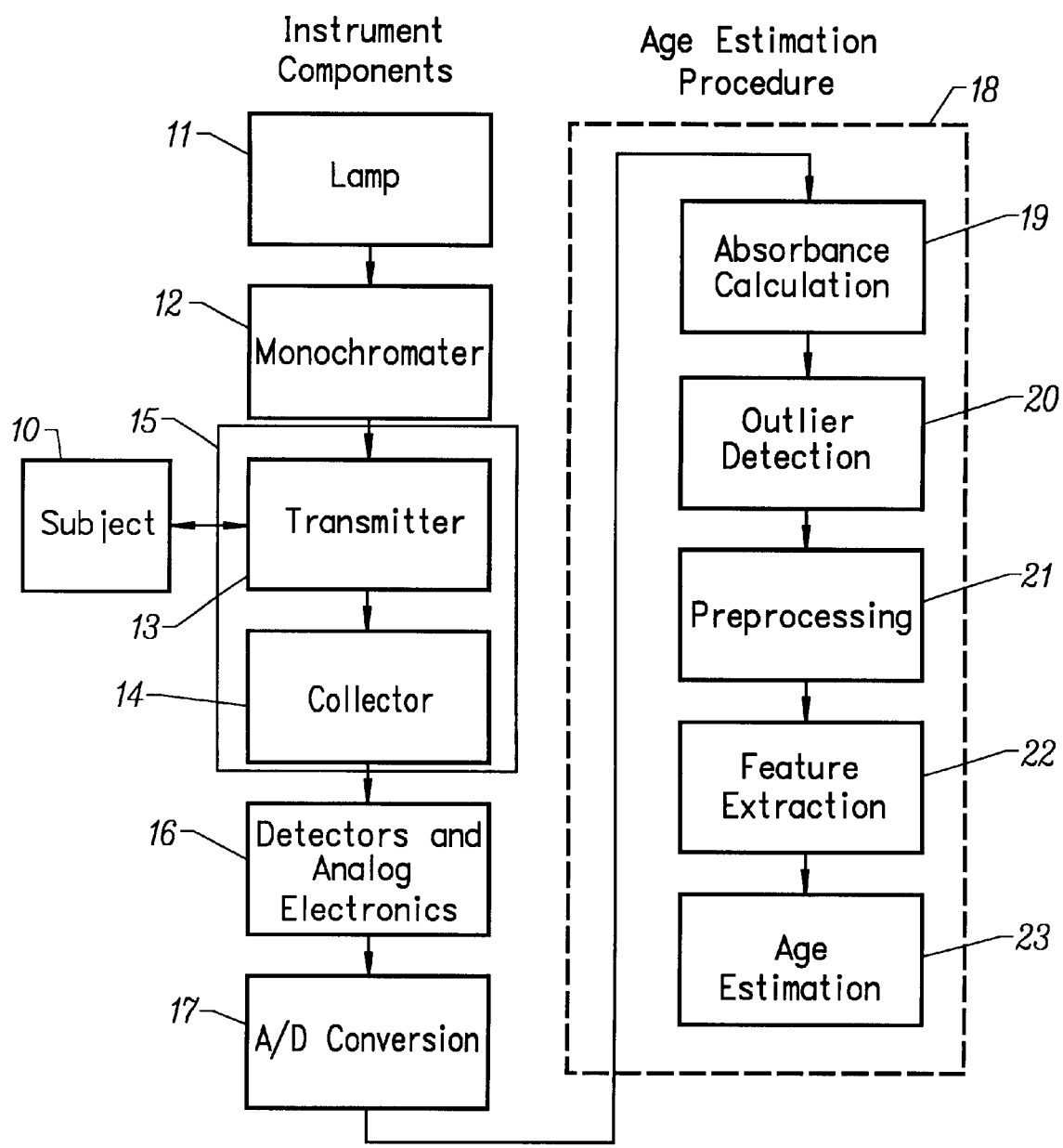
FIG. 1 provides a block diagram of an age estimation apparatus and procedure according to the invention.
Figure 2:
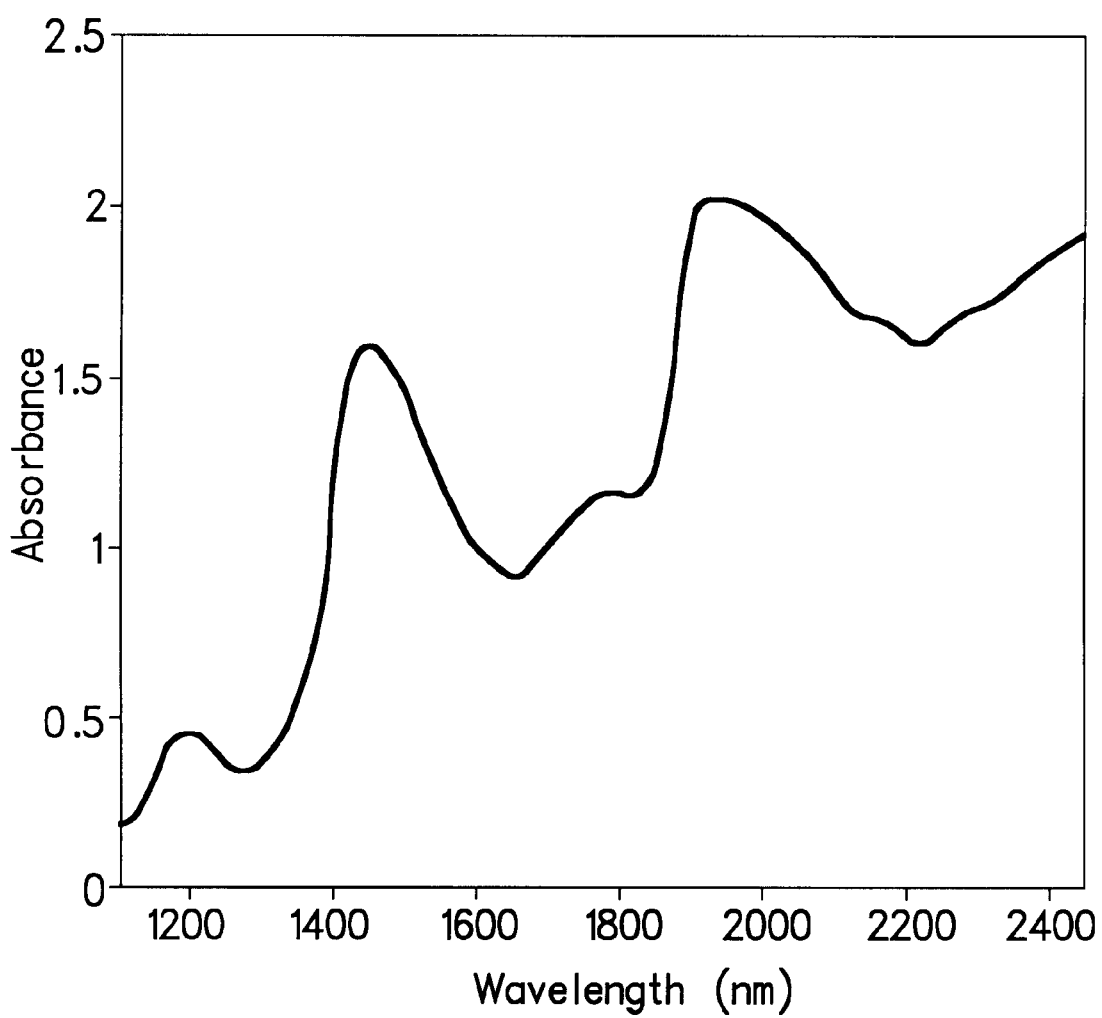
FIG. 2 is a plot of a typical NIR absorbance spectrum of an in vivo sample of skin tissue.

A block diagram of the integrated system is shown in FIG. 1. In the preferred embodiment the instrument employs a quartz halogen lamp 11, a monochromator 12 and InGaAs detectors 16. The detected intensity from the sample is converted to a voltage through analog electronics 16 and digitized through a 16-bit A/D converter 17. The spectrum is passed to the age estimation procedure for processing. First, the absorbance is calculated 19 on the basis of the detected light through—$\log(R/R_o)$ where R is the reflected light and $R_o$ is the light incident on the sample determined by scanning a reference standard. For example, FIG. 2 shows a typical absorbance spectrum collected on an apparatus according to the preferred embodiment. Subsequent processing steps, described below, result in either an apparent age estimate 23 or an apparent age classification 41.

Alternately, the measurement can be accomplished with existing NIR spectrometers that are commercially available including a Perstorp Analytical NIRS 5000 spectrometer or a Nicolet Magna-IR 760 spectrometer. In addition, the measurement can be made by collecting reflected light off the surface of the skin or light transmitted through a portion of the skin, such as the finger or the ear lobe. Further, the use of reflectance or transmittance can replace the preferred absorbance measurement.

Optical Interface

The specific tissue layer sampled is related to the type of ageing. For example, degradation of the upper dermis is related to photo ageing while chronological ageing is distinguished by changes in the lower dermis. See, for example M. Gniadecka and G. Jemec, Quantitative evaluation of chronological ageing and photo ageing in vivo: studies on skin echogenicity and thickness, Br J Dermatol (1998) vol. 139, pp. 815–821.

The upper dermis becomes thicker (solar elastosis) with increased sun exposure and the lower dermis degrades with chronological age. In the present invention the specific tissue layer that is sampled is controlled through the spacing of the point of illumination and the point of light detection by the optical interface (15). The point of illumination is set through a focusing lens or delivered directly via a fiber optic probe. The point of detection is controlled through starring optics or a fiber optic probe. The preferred spacing for the determination of photo ageing is less than 300 $\mu$m. The preferred source to illumination spacing for chronological ageing is 0.3 to 3 mm based on the wavelength region (0.3 mm between 2000 and 2500 nm, 1–2 mm in the 1500–1850 nm range and 3 mm in the 700–1400 nm range).

General Age Estimation Procedure

Figure 3:
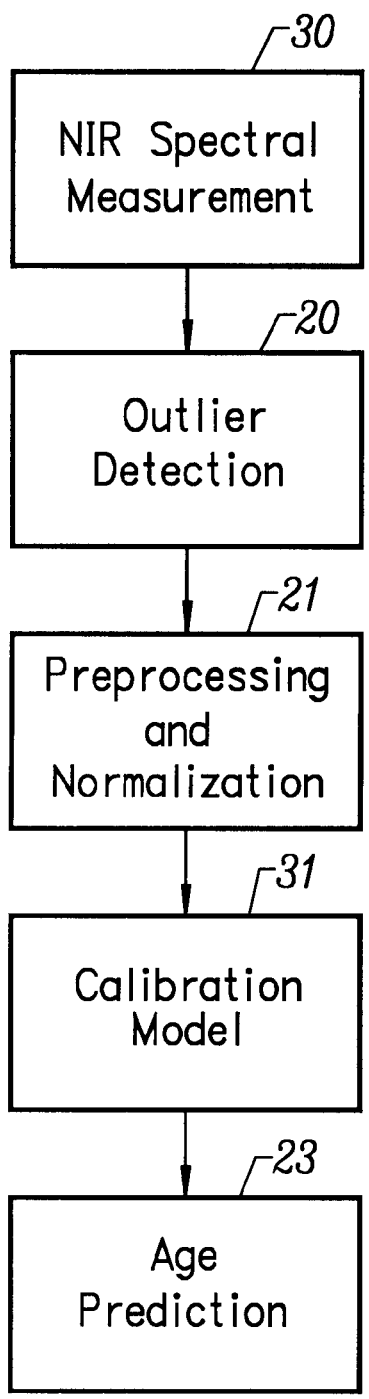
FIG. 3 provides a block diagram of a general procedure for predicting subject age based on NIR spectral measurements according to the invention.

The general procedure for age estimation based on the measured NIR spectrum, shown in FIG. 3, is implemented in a microprocessor 18 that automatically receives the measurement information from the ADC 17. The procedure for age estimation includes the sub-procedures outlier detection 20, preprocessing 21 and estimation 23. Each sub-procedure is performed on the basis of a calibration set of exemplary measurements that includes an absorbance spectrum and a measure of the apparent age (or chronological age or photo-age) of the subject population. Presented below is an overview of the procedure for estimating the apparent age on the basis of spectral measurements. Further details are provided in the subsequent Implementation section, below.

Measurement

The measurement 30 is a spectrum denoted by the vector $m \in \Re^N$ of absorbance values pertaining to a set of N wavelengths $\lambda \in \Re^N$ that span the near infrared (700 to 2500 nm). A typical plot of m versus $\lambda$ is shown in FIG. 2.

Outlier Detection

The outlier detection procedure 20 is a method for detecting invalid measurements due to spectral variations resulting from problems in the instrument, poor sampling of the subject or a subject lying outside the calibration set. The preferred method for the detection of spectral outliers is through a principal component analysis and a further analysis of the resulting residuals. First, the spectrum m is projected onto five eigenvectors, contained in the matrix o, that were previously developed through a principal component analysis (on a calibration set of exemplary absorbance spectra) and are stored in the computer system of the device. The calculation is given by $$xpc_o = \sum_{k=1}^{7} mo_k, \tag{1}$$

and produces the 1 by 5 vector of scores, $xpc_o$ where $o_k$ is the $k^{th}$ column of the matrix o. The residual q is determined according to $$q = m - xpc_o o^T \tag{2}$$

and compared to three times the standard deviation of the expected residual (of the calibration set). If greater, the sample is reported to be an outlier and the age determination procedure is terminated.

Preprocessing

The optional step of preprocessing 21 includes operations such as wavelength selection, scaling, normalization, smoothing, derivatives, filtering and other transformations that attenuate the noise and instrumental variation without affecting the signal of interest. The preprocessed measurement, $x \in \Re^N$, is determined according to $$x = h(\lambda, m) \tag{3}$$

where $h: \Re^{N \times 2} \to \Re^N$ is the preprocessing function. Wavelength selection is performed on the data to eliminate extraneous variables that may bias the calibration or portions of the measured spectrum with a low signal-to-noise ratio. This is performed visually and through an analysis of the noise at each wavelength. The specific preprocessing methods used for age estimation may include wavelength selection, multiplicative scatter correction and derivatives. See, for example P. Geladi, D. McDougall and H. Martens. Linearization and Scatter-Correction for Near-Infrared Reflectance Spectra of Meat, Applied Spectroscopy (1985) vol. 39, pp. 491–500, and A. Savitzky and M. Golay, Smoothing and Differentiation of Data by Simplified Least Squares Procedures, Anal. Chem., vol. 36, no. 8, pp. 1627–1639 (1964).

Estimation

The estimation procedure employs a calibration model 31 that maps the preprocessed spectrum through a linear or nonlinear mapping to an estimate of the age. In the linear case, given the processed spectrum x, and the calibration model coefficients $w_c$, the age estimate is determined according to $$\hat{y} = \sum_{k=1}^{N} w_{c,k} x_k \qquad (4)$$

were $W_{c,k}$ is the $k^{th}$ element of $w_c$ and $\hat{y}$ is the age estimate. One skilled in the art will appreciate that a nonlinear mapping from x to $\hat{y}$ can also be easily specified through artificial neural networks, nonlinear partial-least squares regression or other nonlinear method of calibration.

See, for example H. Martens and T. Naes, *Multivariate Calibration.* New York: John Wiley and Sons, (1989) pp. 419; P. Geladi, D. McDougall and H. Martens. Linearization and Scatter-Correction for Near-Infrared Reflectance Spectra of Meat, Applied Spectroscopy, (1985) vol. 39 pp. 491–500; and Y. Pao, *Adaptive Pattern Recognition and Neural Networks,* Addison-Wesley Publishing Company, Inc., Reading, Mass., (1989).

The preferred model is linear and is constructed through factor analysis to decompose the high dimensional (redundant) data consisting of absorbance, intensity or reflectance measurements at several hundred wavelengths to a few significant factors that represent the majority of the variation within the data set. The factors that capture variation in the spectra that correlate with age are used in the calibration model and the samples are projected into the resulting factor space to produce a set of scores for each sample. Finally, multiple linear regression is applied to model the relationship between the scores of the significant factors and the apparent age 23 of the subject.

General Age Classification Procedure

NIR measurements 30 from tissue samples of varying age can be classified into age groups according to their physical and chemical properties. The procedure for classifying samples according to predefined age groups includes preprocessing 21 the data for feature enhancement, performing a factor analysis for variable reduction and developing a classification calibration on the significant factors. The classification calibration is any mathematical or statistical technique, such as Fisher's Linear Discriminant Analysis, that assigns a label to a sample and, using a decision rule, can determine the population membership of the sample. Methods, such as multiplicative scatter correction and derivatives, are used to enhance features associated with age parameters.

See R. Duda and P. E. Hart, *Pattern Classification and Scene Analysis,* John Wiley and Sons, New York, 1973. Also see P. Geladi, D. McDougall and H. Martens. Linearization and Scatter-Correction for Near-Infrared Reflectance Spectra of Meat, Applied Spectroscopy, (1985) vol. 39, pp. 491–500.

Figure 4:
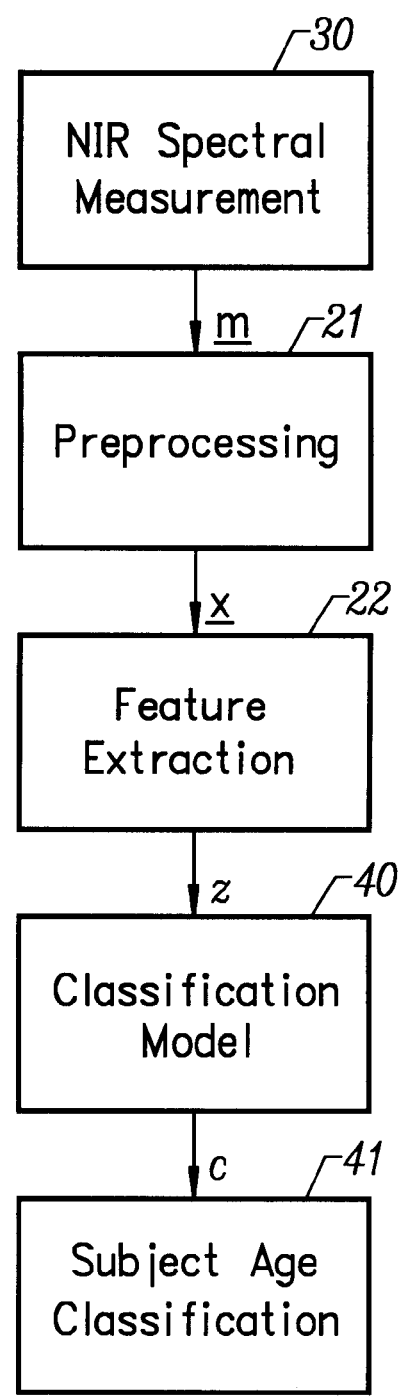
FIG. 4 provides a block diagram of a classification system for determining the age of a subject based on NIR spectral measurements according to the invention.

A factor-based analytical method, such as principal component analysis (PCA), is applied to the preprocessed data in order to reduce the data set down to a few significant age-related factors. The classification calibration is developed using the significant age-related factors. The classification calibration can then be used to determine the membership of a new sample. FIG. 4 is a flow diagram of the basic age classification steps. The general procedure is implemented in a microprocessor 18 that automatically receives the measurement information from the ADC.

Outlier Detection and Preprocessing

The procedures for outlier detection 20 and preprocessing 21 are similar to those defined in the General Age Estimation Section. The specific procedures are optimized on the basis of the calibration set for feature extraction 22 and classification 41 as presented in the Implementation Section, below.

Feature Extraction

Feature extraction 22 determines the salient characteristics of measurements that are relevant for age classification. Feature extraction 22 is any mathematical transformation that enhances a quality or aspect of the sample measurement for interpretation. The purpose of feature extraction 22 is to concisely represent and enhance the properties and characteristics of the tissue measurement site for age classification. In addition, the features provide significant information about the tissue properties they represent and can be used for alternate purposes such as system diagnostics or optimization.

The features are represented in a vector, $z \in \Re^M$ that is determined from the preprocessed measurement through $$z = f(\lambda, x) \qquad (5)$$

where $f: \Re^N \to \Re^M$ is a mapping from the measurement space to the feature space. Decomposing $f(\bullet)$ yields specific transformations, $f_i(\bullet): \Re^N \to \Re^{M_i}$ for determining a specific feature. The dimension, $M_i$, indicates whether the $i^{th}$ feature is a scalar or a vector, and the aggregation of all features is the vector z. When a feature is represented as a vector or a pattern, it exhibits a certain structure indicative of an underlying physical phenomenon.

The individual features are divided into two categories:
abstract, and
simple.

Abstract features do not necessarily have a specific interpretation related to the physical system. Specifically, the scores of a principal component analysis are useful features although their physical interpretation is not always known. (See H. Martens, T. Naes, *Multivariate Calibration,* John Wiley and Sons, New York (1989) pp. 419. For example, the utility of the principal component analysis is related to the nature of the tissue absorbance spectrum. The most significant variation is generally related to the tissue structure, which varies systematically with age. Therefore, the scores from the principal component analysis constitute a valuable set of features in that they provide information that can be used for age determination.

Figure 5A:
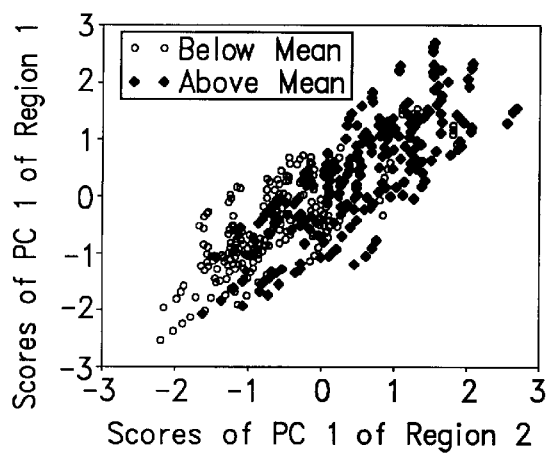
FIG. 5 provides a scatter plot of selected principal component scores showing systematic separation by subject age according to the invention.
Figure 5B:
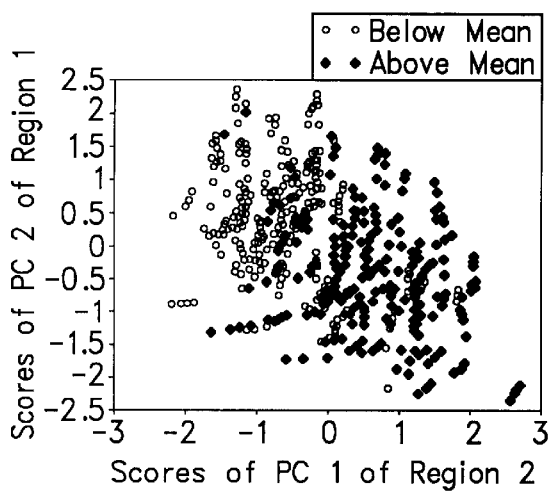
Figure 5C:
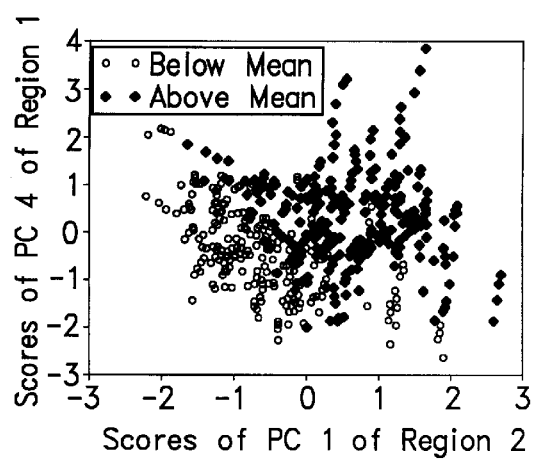

According to a preferred realization of the invention, the use of principal component analysis to represent spectral variation related to age is demonstrated through the Experimental Data Set, more fully described in the Implementation Section, below. The set of spectra, collected on 266 subjects of diverse age and sex, was subjected to principal component analysis in two wavelength regions: Region 1 (1100–1380 nm) and Region 2 (1550–1800 nm). The scores of selected principal components were plotted versus one another as shown in FIGS. 5a, 5b and 5c, with different symbols for data points corresponding to individuals above (old) and below (young) the mean age of 49 years. The scores, representing variation in the spectra, show a pronounced systematic separation according to subject's age. The unmistakable grouping of the data according to age in the scatter plots of FIG. 5 clearly demonstrates the utility of feature extraction through principal component analysis and the possibility of subsequent classification of the subjects according to age. In addition, the correlation between age and the lower numbered principal components indicates that age represents a primary source of variation in the spectra.

Simple features are derived from an a priori understanding of the sample and can be related directly to a physical phenomenon. For example, the thickness of the dermis varies systematically with age and results in specific spectral manifestations. These spectral variations are extracted and enhanced and serve both as a feature for age classification and as a measurement of their respective tissue properties.

Although the full spectrum can be passed to the classification model 40 for age classification 41, a preferred realization of the invention employs either of two specific methods of feature extraction that provide superior classification performance and measurement of other relevant tissue properties:

the scores from factor analysis, and the estimates from partial least squares (PLS) regression.

The detailed implementation of the procedure for extracting these features on the basis of a calibration set is provided in the next section, below.

Crisp Classification

The classification 41 of the subject's age on the basis of the extracted features is performed through a classification step that involves a mapping and a decision. The mapping step is given by $$L = f(z) \qquad (6)$$

where L is a scalar that can be used to measure the distance from the predefined age categories. For example, two values, $L_{old}$ and $L_{young}$, associated with the representative or mean value of L for the "old" and "young" categories respectively are predefined, and the class assignment is based on the closeness of L to $L_{old}$ and $L_{young}$. For example, the distance of L from a previously defined class boundary means that classes can be measured by $$d_{old} = |L_{old} - L|$$

$$d_{young} = |L_{young} - L| \qquad (7)$$

The decision is made as follows:

if $d_{old} > d_{young}$ then the apparent age of the tissue is classified as "old,"

if $d_{old} > d_{young}$ then the apparent age of the tissue is classified as "young."

The mapping and decision limits are determined from a calibration set of exemplary features and corresponding apparent age reference values through a classification calibration procedure. Commonly known methods of classification calibration include linear Discriminant analysis, SIMCA, k nearest-neighbor, fuzzy classification and various forms of artificial neural networks. Furthermore, one skilled in the will appreciate that more than two distinct classes for age can be defined with an upper limit based on the accuracy of the measurement device.

See, for example R. Duda and P. Hart, *Pattern Classification and Scene Analysis,* John Wiley and Sons, New York, (1973); S. Wold and M. Sjostrom. SIMCA: A method for analyzing chemical data in terms of similarity and analogy, Chemometrics: Theory and Application, ed. B. R. Kowalski, ACS Symposium Series, vol. 52, (1977); J. Bezdek and S. Pal, eds., *Fuzzy Models for Pattern Recognition,* IEEE Press, Piscataway, N.J., (1992); J. Keller, M. Gray and J. Givens. A Fuzzy K nearest Neighbor Algorithm, IEEE Transactions on Systems, Man, and Cybernetics, Vol. SMC-15, No. 4, pp. 580–585, (July/August, 1985); and Y. Pao, *Adaptive Pattern Recognition and Neural Networks,* Addison-Wesley Publishing Company, Inc., Reading, Mass., (1989).

Fuzzy Classification

While statistically based class definitions provide a set of classes applicable to age classification, the apparent age of a tissue sample and the resulting spectral variation change over a continuum of values. Consequently, the natural variation in the spectra results in class overlap. Distinct class boundaries based on age do not exist and many measurements are likely to fall between classes and have a statistically equal chance of membership in any of several classes. Hence, "hard" class boundaries and mutually exclusive membership functions may be insufficient to model the variation found in a target population.

A more versatile method of class assignment is based on fuzzy set theory. (See J. Bezdek, and S. Pal, eds., *Fuzzy Models for Pattern Recognition,* IEEE Press, Piscataway, N.J., (1992); C. Chen, ed., *Fuzzy Logic and Neural Network Handbook,* IEEE Press, Piscataway, N.J. (1996); and L. Zadeh, Fuzzy Sets, Inform. Control, vol. 8, pp. 338–353, (1965).

Generally, membership in fuzzy sets is defined by a continuum of grades and a set of membership functions that map the feature space into the interval [0,1] for each class. The assigned membership grade represents the degree of class membership with "1" corresponding to the highest degree. Thus, a sample can simultaneously be a member of more than one class.

The mapping from feature space to a vector of class memberships is given by $$c_k = f_k(z), \qquad (8)$$

where k=1,2, . . . P, $f_k(\bullet)$ is the membership function of the $k^{th}$ class, $c_k \in [0,1]$ for all k and the vector $c \in \Re^P$ is the set of class memberships. An example of the general equation employed to represent a membership function is $$y = e^{\frac{-1}{2\sigma^2}(z-\bar{z})^2} \qquad (9)$$

where y is the degree of membership in a sub-set, z is the feature used to determine membership, $\bar{z}$ is the mean or center of the fuzzy sub-set and σ is the standard deviation. However, one skilled in the art will appreciate that the suitable membership function is specific to the application.

The membership vector provides the degree of membership in each of the predefined classes and can be used for blood analyte prediction as disclosed in the parent application to the current application, S. Malin, T. Ruchti, An Intelligent System For Noninvasive Blood Analyte Prediction, U.S. patent application Ser. No. 09/359,191, (Jul. 22, 1999). Alternately, the degree of class membership can be used to calculate the apparent age, photo-age or chronological age of an individual with a suitable function for defuzzification. The defuzzification function can be determined as described by Bezdek, et al (See J. Bezdek, and S. Pal, eds., *Fuzzy Models for Pattern Recognition.* IEEE Press, Piscataway, N.J., (1992). Also see the parent application to the current application, as above.) Alternately, a calibration set of exemplary spectral measurements and associated age reference values can be used to determine a calibration model for mapping the class membership to an estimate of the selected age.

Implementation Details

Various realizations of the invention, comprising specific procedures for age estimation and classification are described in detail below.

Experimental Data Set

A study was performed to generate calibration and validation data for the procedures subsequently described. Two Hundred sixty-six human subjects of diverse age, sex and ethnicity were recruited at a local health care facility, and detailed demographic information about each participant was recorded. Four replicate absorbance spectra were measured on each subject's forearm with the previously described spectrometer apparatus according to the preferred embodiment. One sample per each participant was included in the data set. Henceforth, the total set of spectra and demographic information shall be referred to as the "Experimental Data Set."

While this is a specific experiment aimed at the determination of a suitable set for calibrating the age determination apparatus, one will readily appreciate that for different subjects and for different target performance levels other experiments with smaller or larger subject populations would be performed. Moreover, experiments specific to photo ageing versus chronological ageing would replace this experiment given a different target set of age estimates.

Estimation

Two implementations of the age estimation procedure are described in the following sub-sections differing by the wavelength region of the absorbance spectrum applied.

Age Estimation 1 (1100–1400 nm)

In the first implementation, the procedure outlined in FIG. 3 was employed. The (PCA q-residual) outlier analysis was performed as described above and 36 samples were removed due to unusually high residuals. No preprocessing was applied and the wavelength region was limited to 1100–1400 nm to ensure sampling of the lower dermis. While sampling of the subcutaneous tissue also occurs in this wavelength region, the magnitude of the fat absorption features is indicative of the absorption characteristics of the dermis and epidermis and provides an indirect measurement of the target absorption characteristics. Partial least squares (PLS) regression with 17 factors was applied to the entire data set to develop a calibration model. (See P. Geladi and B. Kowalski, Partial least-squares regression: a tutorial, Analytica Chimica Acta, vol. 85, pp. 1–17 (1986).

Figure 6:
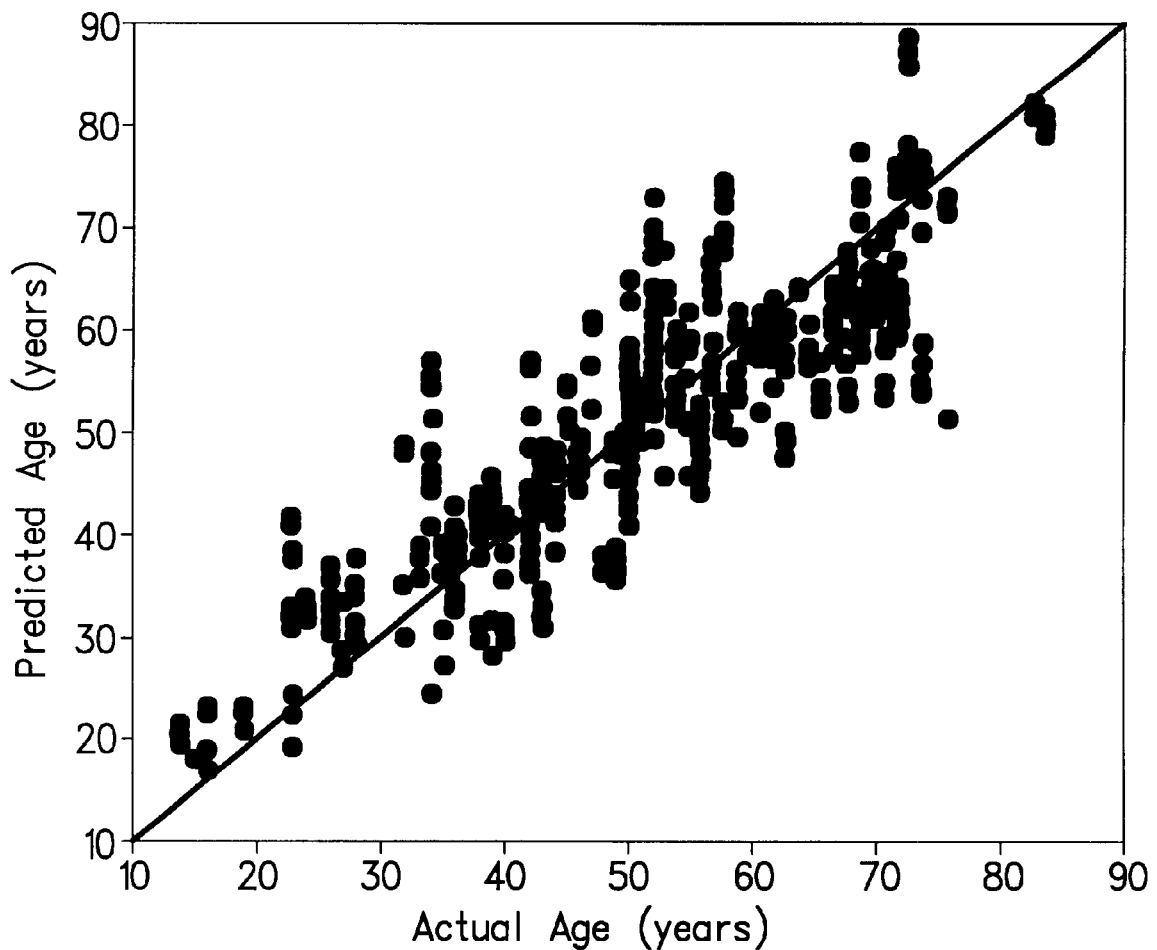
FIG. 6 is a graph of estimated age versus actual chronological age according to the invention.

The performance of the estimation model was evaluated through cross-validation using a "leave-one-out" strategy and calculating the standard error values. The cross-validation procedure was used iteratively to estimate the age of each sample by using all other samples to construct the calibration model. After each sample had been predicted the standard error of cross-validation (SECV) was computed as the root mean square error of the cross-validation age estimates. The results of the estimated chronological age (through cross-validation) versus the actual age are shown in FIG. 6. The standard error of prediction is 7.8 years and the plot shows a clear statistically significant level of estimation. The error in prediction may be attributed to two phenomena. First, the rate of chronological ageing in different individuals is not necessarily the same. As a result, the reference values contain error by definition. Secondly, photo-damage to the upper dermis represents a confounding effect that may limit the accuracy of the estimation model.

Age Estimation 2 (1500–2400 nm)

In this implementation the estimation of age 23 is performed using partial least squares (PLS) regression on upper wavelength regions of the absorbance spectra. While the lower wavelength region used in Age Estimation Method One targets primarily the dermis and subcutaneous tissue, the high absorbance of water prevents significant sampling of the subcutaneous tissue at upper wavelengths. Since age related parameters manifest themselves most distinctly in the dermis and epidermis of the tissue, limiting the wavelength range to the 1500 to 2400 nm region limits potential interferences contributed by the subcutaneous tissue.

Outlier analysis was applied to the data set as previously described. The remaining samples were split into calibration (60%) and test (40%) sets. No feature enhancement or preprocessing techniques were applied and cross-validation validation was used on the calibration set to determine that eight was the optimal number of factors for feature extraction. The calibration was then developed using the calibration set and applied to the test set for validation.

The test set had a standard error of prediction of 8.0 years. The cause of the error in the prediction can be explained similarly to that for Age Estimation Method One: a disparity between the actual chronological age of the subject and the apparent age of the tissue; consequently, a subject's skin condition may resemble that of the skin of a person several years older due to photo ageing. effects. Thus, in a person using a photo-damage-reversing drug, periodically predicting the apparent age of the skin throughout the course of treatment would be an effective way to monitor the performance of the drug.

Classification

The classification 41 of subjects according to age was implemented using three different approaches. The first two involve a crisp classification system in which distinct class boundaries are defined and each sampled absorbance spectrum has membership in only one class. The third method involves the use of a fuzzy system to arrive at an estimate of the degree of membership in each of several predefined classes for each sample.

In the application of this system to the prediction of blood analytes, the accuracy of chronological age prediction is not the most important element but rather the characterization of the apparent age of the sampled tissue volume. Nevertheless, one skilled in the art will appreciate that the following methods and procedures are easily adapted to other applications.

Age Classification 1. (Crisp 1100–1800 nm)

Figure 7:
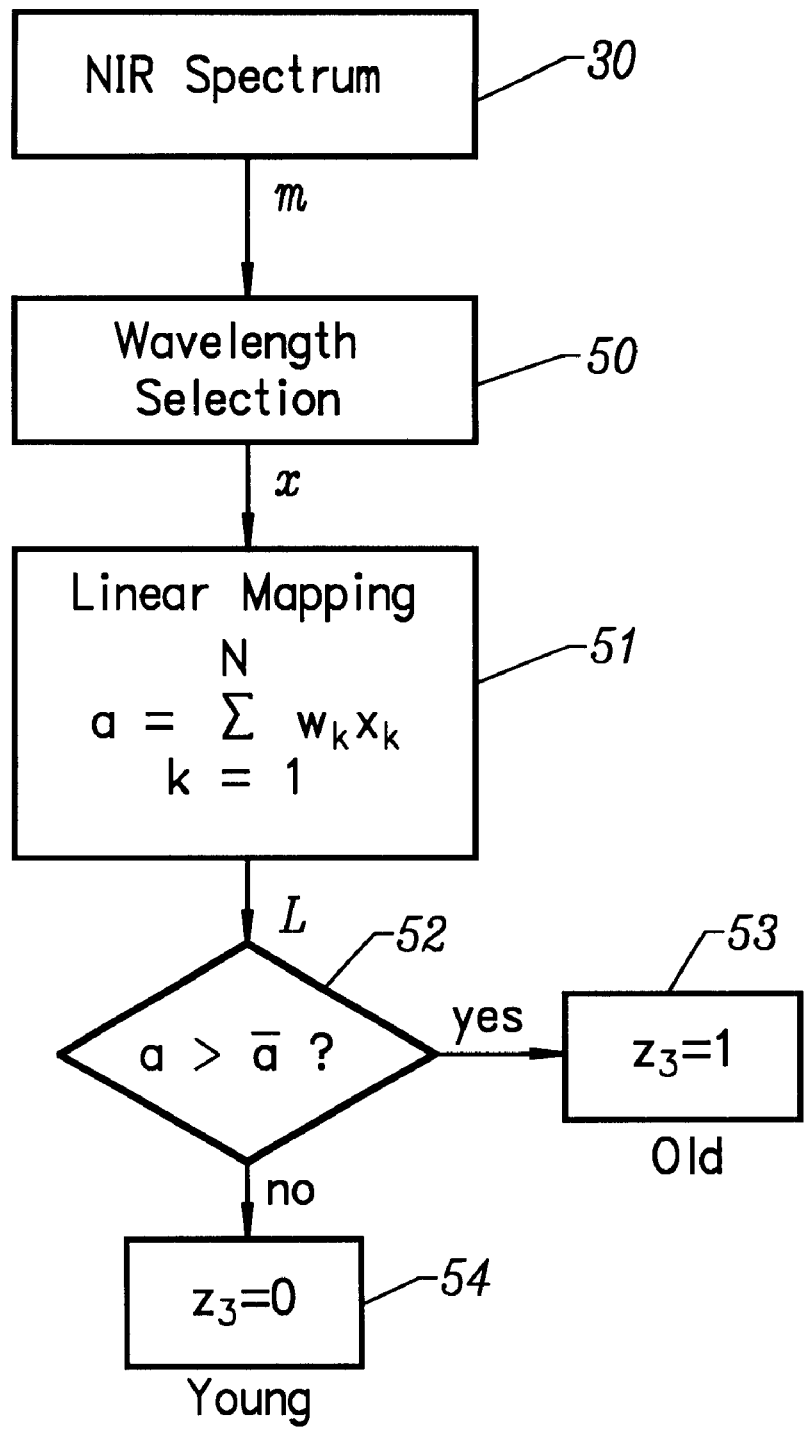
FIG. 7 is a block diagram of a first procedure for classification of subjects into age categories according to the invention.

The first age classification implementation is depicted in FIG. 7 and involves the prediction of the subject's age using a linear model developed through partial least squares regression. In the current implementation, the wavelength range of the spectrum 30 is truncated to the regions 1100–1380 nm and 1550–1800 nm in the wavelength selection process 50. Next, the subject's age is predicted through a calibration model. The model, developed through PLS on a calibration set of exemplary samples, consists of a set of coefficients contained in the vector w 51 and is applied as shown in FIG. 7 to produce the age prediction, a 52. The subject is classified as "young" 54 or "old" 53 by comparing a 52 to the mean age $\bar{a}$=49 as detailed in the figure. One skilled in the art will appreciate that more than two distinct classes can be defined with an upper limit based on the accuracy of the measurement device.

Using the Experimental Data Set, the PLS calibration model was developed using 20 factors. The classification accuracy was evaluated through cross-validation in which groups of 12 samples were iteratively left out of the calibration model. The accuracy of age classification was found to be 79%. The reason for the error is attributable to the continuum of chronological ages and skin tissue properties that were measured using a classification with crisp boundaries. In Age Classification 2 the boundary is modified by removing samples from the calibration that represent chronological ages in between the two main old and young categories.

Age Classification 2 (Crisp 1500–2500 nm)

Figure 8:
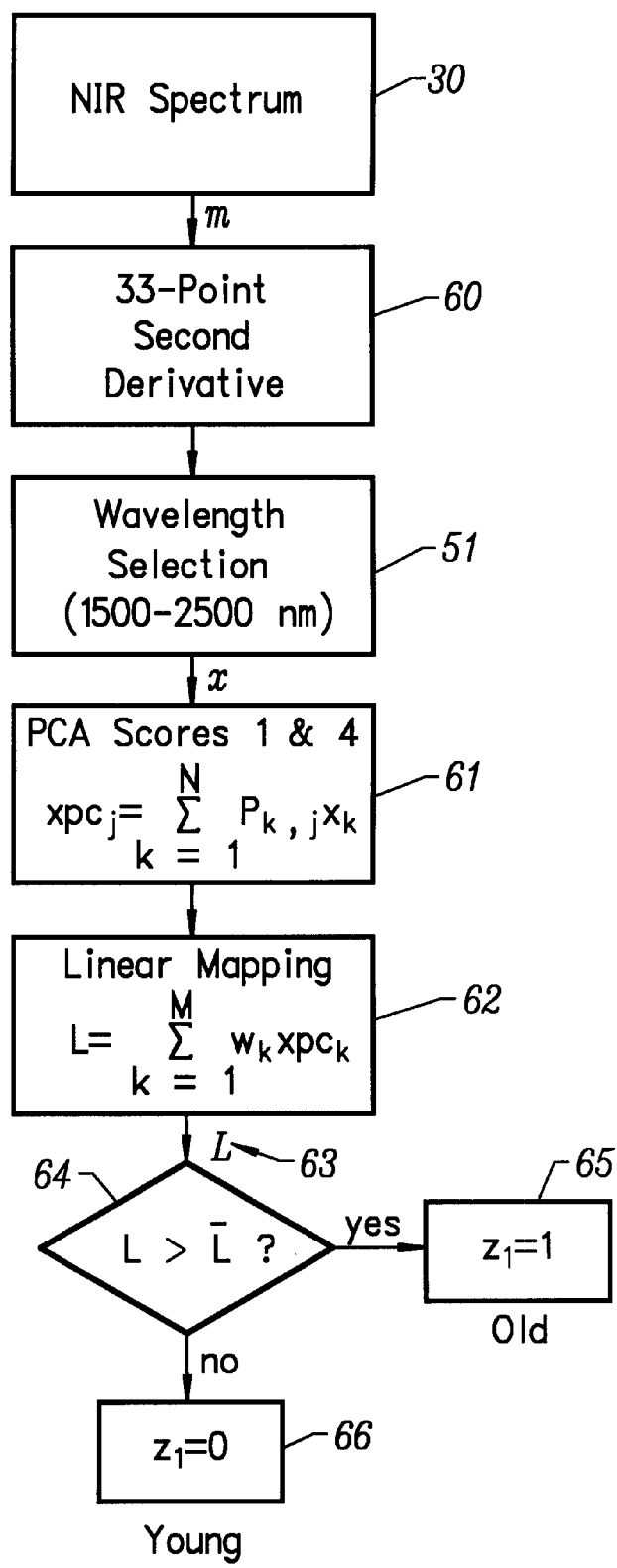
FIG. 8 is a block diagram of a second procedure for classification of subjects into age categories according to the invention.
Figure 9:
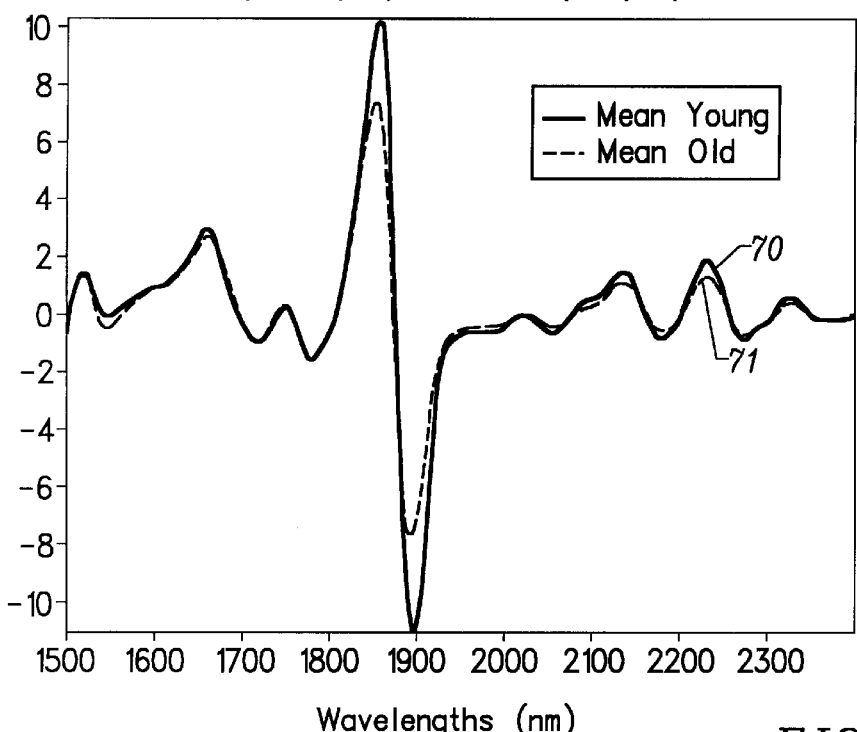
FIG. 9 is a plot of the mean second derivative spectra of the separate age categories of FIG. 8 according to the invention.
Figure 10:
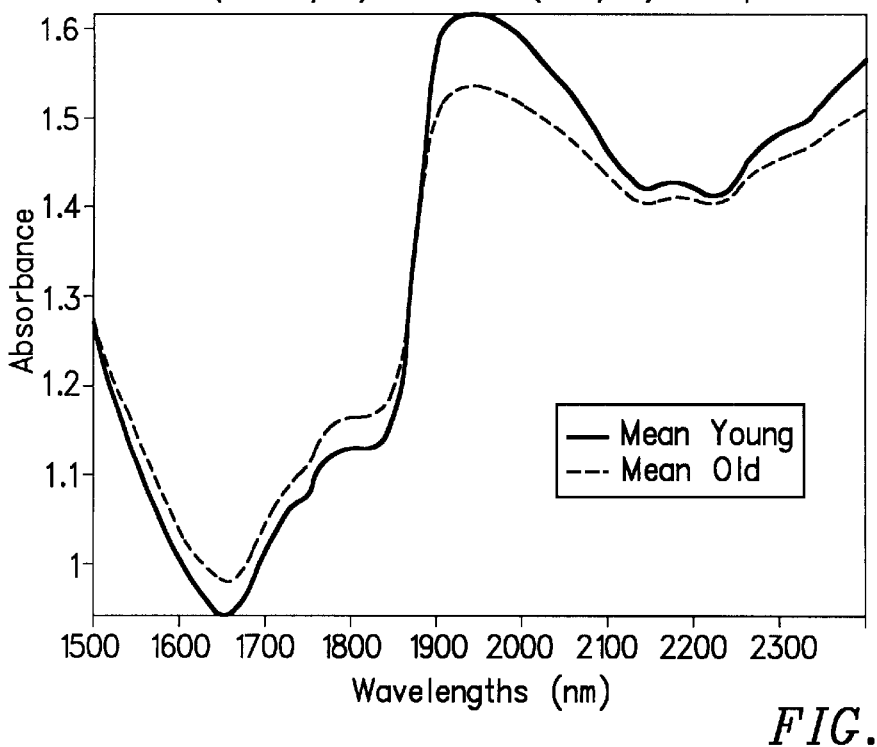
FIG. 10 is a plot of the mean spectra of the separate age categories of FIG. 8 according to the invention.
Figure 11:
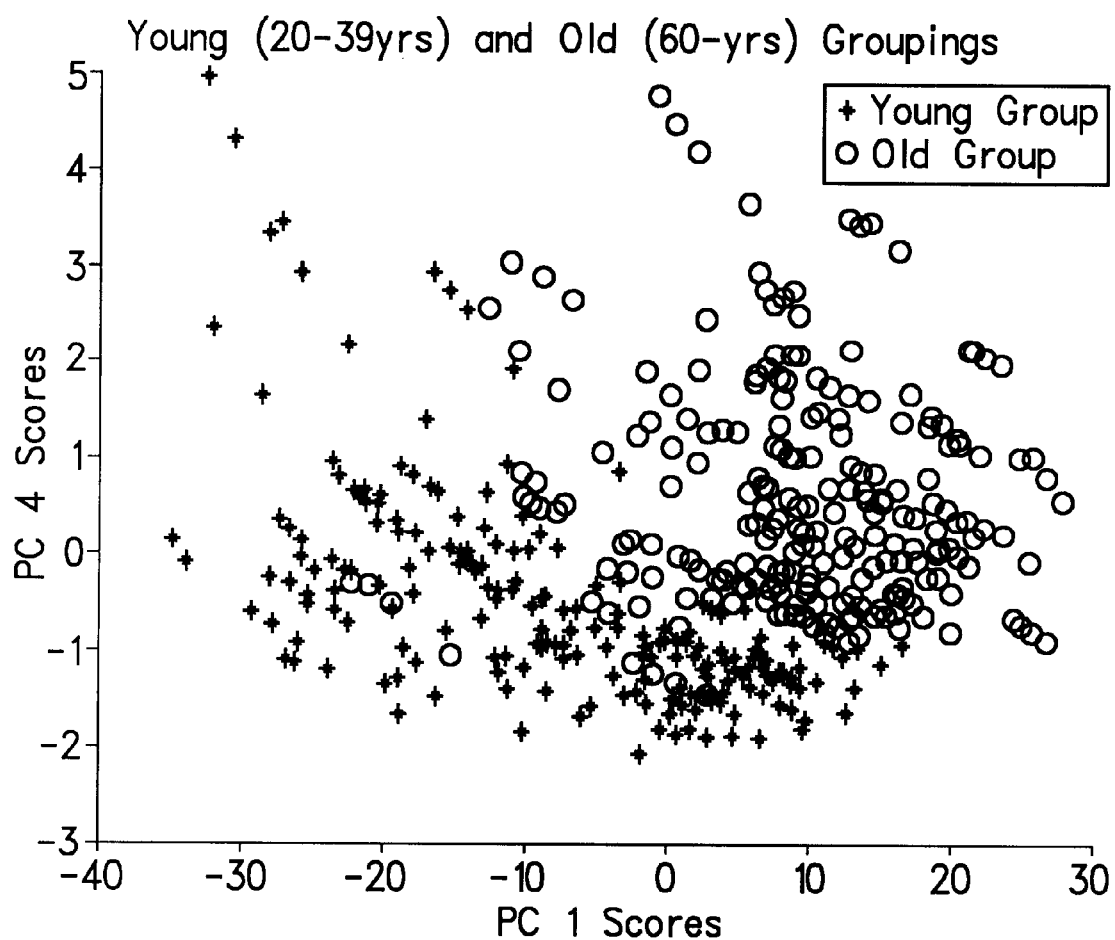
FIG. 11 is a scatter plot showing the separation of principle component scores associated with young and old subjects according to the invention.

The second age classification procedure is detailed in FIG. 8 and was developed based on the calibration set described in the Age Estimation 2 Section. The procedure provides two groups: a young group that includes ages from 20 to 39 years old and an old group which ranged from 60 to 84 years old. The middle age range was left out in order to get a more distinct separation between age groups. A 33-point second Savitzky-Golay derivative 60 (see A. Savitzky and M. Golay. Smoothing and Differentiation of Data by Simplified Least Squares Procedures, Anal. Chem., vol. 36, no. 8, pp. 1627–1639, (1964). was applied to the spectral data 30 to enhance the variation in the mean spectra 70, 71 due to age (see FIG. 9). Referring now to FIG. 10, the largest separation between the mean spectra 70, 71 of the two age groups was observed over the wavelength regions of 1500 to 2500 nm. Thus, this was the wavelength region selected 51 for further analysis. A principal component analysis (PCA) was applied to the spectral data 30 over the selected wavelength region. The scores from the PCA were plotted against one another to reveal clustering of the data related to age. As shown in FIG. 11, two clusters corresponding to the two age groups formed when the scores from principal component one was plotted against scores from principal component four 61. These two groups can be used to represent tissue with young and old characteristics. Using these two distinct age groups a classification model was developed from the age significant scores and used to classify the apparent age of new samples.

The procedure of FIG. 8 uses two eigenvectors associated with principal components 1 and 4 to determine the scores, $xpc_1$ and $xpc_2$, of each sample. A Discriminant function is applied to classify the subjects based on the two features contained in m through the equation shown in the figure to produce the scalar, L 63. This result is compared to $\overline{L}$ 64, the center between the two classes. If $L > \overline{L}$ then the subject is classified as a old 65. If not, the spectrum is classified as belonging to the young class 66. Using the calibration set, the linear mapping 62 of FIG. 8 was developed via linear Discriminant analysis (see Duda, R. O. and P. E. Hart, Pattern Classification and Scene Analysis, John Wiley and Sons, New York, 1973) and. produced the following weight vector $$w = [0.1198 \ 0.9928] \quad (10)$$

From the calibration set, the mean value for L was found to be 0.1131. Using these parameters in conjunction with the procedure of FIG. 8 allowed age prediction in the test set with 90% accuracy.

Age Classification 3 (Fuzzy)

The final procedure for age classification is the utilization of a set of fuzzy membership functions that determine the degree of membership in the categories young, middle aged and old based on the feature defined in the Age Classification 1 Section. The set of membership functions 91,92,93 shown in FIG. 12, are Gaussian functions given by $$y = e^{\frac{-1}{2\sigma^2}(z - \bar{z})^2} \quad (11)$$

where y is the degree of membership in a sub-set, z is the feature used to determine membership (the PLS age prediction), $\bar{z}$ is the mean or center of the fuzzy sub-set and σ is the standard deviation. However, one skilled in the art will appreciate that the suitable membership function is specific to the application. The mean and standard deviation associated with each of the three categories were determined based on the target population of subjects in the Experimental Data Set and are listed in Table 1.

TABLE 1

Figure 12:
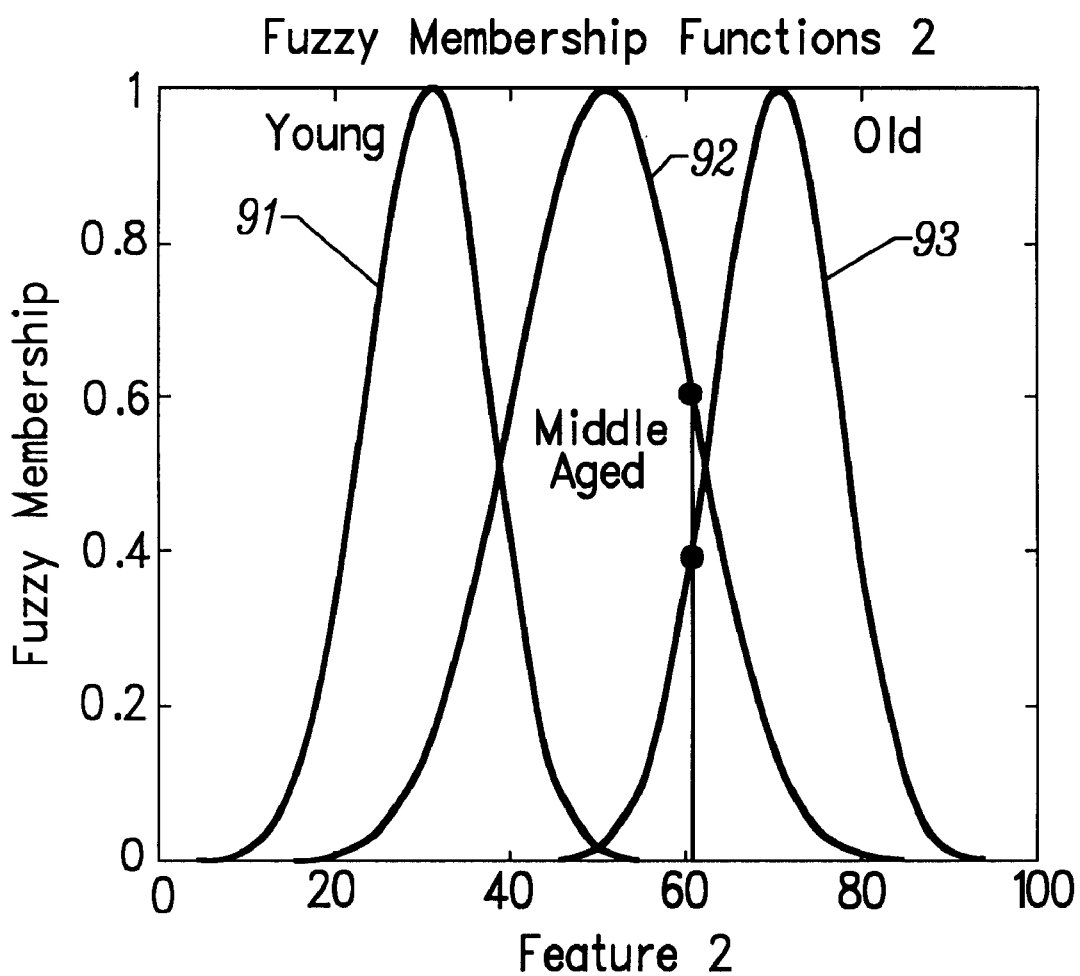
FIG. 12 is a plot of a membership function for a fuzzy classification of subjects by age according to the invention.

Parameters of Membership Functions plotted in FIG. 12.

| Sub-Set Category | Mean (Years) | Standard Deviation (Years) |
|---|---|---|
| Young | 30 | 7 |
| Middle Aged | 50 | 10 |
| Old | 70 | 7 |

Values for the feature inputs to the membership functions that are unusually high or low fall outside that expected range of the sub-sets and are assigned low membership values. This information is used to indicate that the subject's apparent age is outside of the previously examined population and is used for outlier analysis. For the current implementation, when y<0.1 for all sub-sets, the prediction is assigned a low confidence level.

The resulting class memberships are suitable for use in categorization for blood analyte prediction as described in the parent application to the current application: An intelligent system for noninvasive blood analyte prediction, S. Malin, T. Ruchti, U.S. patent application Ser. No. 09/359, 191, filed Jul. 22, 1999. The membership functions described have been designed for a specific population of subjects and cannot be generalized to all potential individuals. The invention, nevertheless, is directed to the arbitrary use of membership functions to assign a degree of membership in a given class to a subject for blood analyte prediction.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

What is claimed is:

1. A method for noninvasively determining the apparent age of a tissue sample in vivo, comprising the steps of:

measuring the NIR absorption spectrum of said tissue sample;

detecting outliers, wherein said outliers are invalid measurements caused by spectral variation due to any of instrument malfunction, poor sampling, and subjects outside of a calibration set;

preprocessing, wherein said preprocessing step includes one or more transformations that attenuate noise, and instrumental variation without affecting the signal of interest, including wavelength selection, scaling, normalization smoothing derivatives, and filtering; and estimating the apparent age of said tissue sample based on said NIR spectrum.

2. The method of claim 1, wherein said NIR region comprises a range of about 700 to about 2500 nm.

3. The method of claim 1, wherein said spectrum is denoted by a vector $m \in \Re^N$ of absorbance values pertaining to a set of N wavelengths $\lambda \in \Re^N$.

4. The method of claim 1, wherein said outlier detection step employs principal components analysis and residual analysis to detect spectral outliers.

5. The method of claim 4, wherein said outlier detection step further comprises the steps of:

projecting a spectrum m onto a plurality of eigenvectors, contained in a matrix o, said matrix o being previously developed through principal components analysis of said calibration set, where $$xpc_o = \sum_{k=1}^{7} mo_k,$$

and where $o_k$ is the $k^{th}$ column of the matrix o; determining the residual q, according to $$q = m - xpc_o o^T$$

comparing said residual q to three times the standard deviation of the residual of said calibration set; and reporting said sample as an outlier if q is greater.

6. The method of claim 1, wherein said preprocessed measurements are denoted by a vector $X \in \Re^N$, and wherein said vector is determined according to $$x = h(\lambda, m)$$

and wherein a preprocessing function is $h: \Re^{N \times 2} \to \Re^N$.

7. The method of claim 1, wherein said age estimation step further comprises the step of:
providing a calibration model to map said preprocessed spectrum through a mapping to an estimate of age.

8. The method of claim 7, wherein said calibration model comprises NIR tissue measurements and chronological ages of an exemplary subject population.

9. The method of claim 7, wherein said mapping is linear.

10. The method of claim 7, wherein said age estimate is determined according to $$\hat{y} = \sum_{k=1}^{N} w_{c,k} x_k;$$

given the preprocessed spectrum x, and the calibration model $w_c$, where $W_{c,k}$ is the $k^{th}$ element of $w_c$ and $\hat{y}$ is the age estimate.

11. The method of claim 10, wherein said calibration model employs factor analysis to decompose a high-dimensional (redundant) data set comprising absorbance, intensity or reflectance measurements at a plurality of wavelengths to significant factors representing the majority of variation within said data set; and
wherein said calibration model includes factors that capture variation in said spectra correlated with variation in subject age.

12. The method of claim 10, further comprising the steps of:
projecting said samples into a resulting factor space to produce a set of scores for each sample; and
applying multiple linear regression to model the relationship between said scores and apparent age of said subject.

13. The method of claim 7, wherein said mapping is non-linear.

14. The method of claim 13, wherein said non-linear mapping is specified through any of artificial neural networks and non-linear partial least squares regression.

15. A method for non-invasively determining the apparent age of a tissue sample in vivo comprising the steps of:
providing a calibration set of exemplary measurements;
measuring the NIR absorption spectrum of said tissue sample;
detecting outliers, wherein said outliers are invalid measurements caused by spectral variation due to any of instrument malfunction, poor sampling, and subjects outside of said calibration set; and
estimating the apparent age of said tissue sample based on said NIR absorption spectrum.

16. A method of classifying a subject according to age based on noninvasive NIR measurements, comprising the steps of:
providing a calibration set of exemplary measurements;
measuring the NIR absorption spectrum of said tissue sample;
detecting outliers, wherein said outliers are invalid measurements caused by spectral variation due to any of instrument malfunction, poor sampling, and subjects outside of said calibration set;
preprocessing, wherein said preprocessing step includes at least one transformation that attenuates noise and instrumental variation without affecting the signal of interest, including wavelength selection, scaling, normalization, smoothing, derivatives, and filtering,
extracting features, whereby factors of measurements relevant to age classification are determined; and
classifying said sample according to predefined age groups.

17. The method of claim 16, wherein said feature extraction step comprises any mathematical transformation that enhances a quality or aspect of said sample measurement for interpretation to represent concisely the properties and characteristics of the tissue measurement site for age classification.

18. The method of claim 17, wherein said feature extraction step employs scores from factor analysis.

19. The method of claim 17, wherein said feature extraction step employs partial least squares regression.

20. The method of claim 17, wherein said features are represented in a vector, $z \in \Re^M$ that is determined from a preprocessed measurement through:

$$z = f(\lambda, x)$$

where $f: \Re^n \to \Re^m$ is a mapping from a measurement space to a feature space, wherein decomposing $f(\bullet)$ yields specific transformations, $f(\bullet): \Re^n \to \Re^m_i$ for determining a specific feature, wherein the dimension $M_i$ indicates whether an $i^{th}$ feature is a scalar or a vector and an aggregation of all features is the vector z, and wherein a feature exhibits a certain structure indicative of an underlying physical phenomenon when said feature is represented as a vector or pattern.

21. The method of claim 20, wherein individual features are divided into two categories comprising:
abstract features that do not necessarily have a specific interpretation related to a physical system; and
simple features that are derived from an a priori understanding of a sample and that can be related directly to a physical phenomenon.

22. The method of claim 21, wherein spectral variations due to changes in dermal thickness corresponding with age are extracted and enhanced, and wherein said variations serve as a feature for age classification and measurement of tissue properties.

23. The method of claim 18, further comprising the step of:
employing factor-based methods to build a model capable of representing variation in a measured absorbance spectrum related to subject age, wherein projection of a measured absorbance spectrum onto said model constitutes a feature that represents spectral variation related to subject age.

24. The method of claim 16, wherein said classification step further comprises the steps of:
   measuring the similarity of at least one feature to predefined age categories; and
   assigning membership to one of said predefined categories.

25. The method of claim 24, wherein said assigning step uses mutually exclusive classes and assigns each sample to one class.

26. The method of claim 24, wherein said assigning step uses a fuzzy classification system that allows class membership in more than one class simultaneously.

27. The method of claim 25, wherein said assigning step further comprises the steps of:
   mapping said sample to one of said predefined classes; and
   applying a decision rule to assign class membership.

28. The method of claim 27, wherein said mapping step is given by:

$$L = f(z)$$

where L is a scalar that measures distance of a sample from the predefined age categories.

29. The method of claim 28, wherein said age categories are "old" and "young" and where $L_{old}$ corresponds to a representative value for said "old" class and $L_{young}$ corresponds to a representative value for said "young class"; and wherein said class assignment is based on the closeness of L to $L_{old}$ and $L_{young}$.

30. The method of claim 29, wherein a distance $d_{old}$ of L to $L_{old}$ is measured by $$d_{old} = |L_{old} - L|,$$

and wherein a distance $d_{young}$ of L to $L_{young}$ is measured by $$d_{young} = |L_{young} - L|.$$

31. The method of claim 29, wherein said decision rule is:
   if $d_{old} < d_{young}$, then the apparent age of the sample is classified as "old;" and
   if $d_{old} \geq d_{young}$, then the apparent age of the sample is classified as "young".

32. The method of claim 27, wherein limits for said mapping and decision rule are determined from a calibration set of exemplary measurements and corresponding apparent age reference values through a classification calibration procedure.

33. The method of claim 32, wherein said classification calibration procedure comprises any of linear Discriminant analysis, SIMCA, k nearest neighbor, fuzzy classification and artificial neural networks.

34. The method of claim 26, wherein class membership is defined by a continuum of grades, and wherein a set of membership functions map a feature space into an interval [0,1] for each class and wherein an assigned grade represents a degree of class membership, and wherein a grade of "1" represents the highest degree of class membership.

35. The method of claim 34, wherein the mapping from the feature space to a vector of class memberships is given by:

$$c_k = f_k(z)$$

where $k=1,2,\ldots P$, and where $f_k(\bullet)$ is the membership of the $k^{th}$ class, and where $ck_k \in [0,1]$ for all k, and where the vector $c \in \mathfrak{R}^P$ is the set of class memberships.

36. The method of claim 35, wherein a membership function is represented by $$y = e^{\frac{-1}{2\sigma^2}(z-\bar{z})^2},$$

where y is the degree of membership in a fuzzy sub-set, z is the feature used to determine membership $\bar{z}$ is the center of a fuzzy subset, and σ is the standard deviation.

37. The method of claim 35, wherein said membership vector provides the degree of class membership in each of said predefined classes.

38. The method of claim 1, further comprising the step of performing a blood analyte prediction based on said age estimate.

39. The method of claim 15, further comprising the step of performing a blood analyte prediction based on said age estimate.

40. The method of claim 16, further comprising the step of performing a blood analyte prediction based on said age classification.

41. An apparatus for non-invasively estimating the relative age of a subject comprising:
   means for generating near infrared (NIR) energy;
   means for separating said generated NIR energy into a plurality of wavelength regions;
   an optical interface comprising:
      means for transmitting said NIR energy from said wavelength separating means towards a target measurement site on a subject; and
      means for collecting NIR energy emanating from said measurement site;
   means for detecting said collected energy and converting said collected energy to a voltage;
   means for converting said voltage to a digital value; and
   means for analyzing said digital value whereby said analysis results in an estimate of said subject's relative age.

42. The apparatus of claim 41, wherein said energy source transmits light in the wavelength range of about 700 nm to 2500 nm.

43. The apparatus of claim 42, wherein said energy source is an LED array or a quartz halogen lamp.

44. The apparatus of claim 41, wherein said wavelength separating means is a monochromator or an interferometer.

45. The apparatus of claim 41, wherein said wavelength separating means comprises successive illumination through an LED array.

46. The apparatus of claim 41 wherein said transmission means is a light pipe, a fiber-optic probe, a lens system, or a light-directing mirror system.

47. The apparatus of claim 41, wherein said energy collecting means comprises at least one starring optical detector.

48. The apparatus of claim 41, wherein said energy collecting means comprises at least one fiber-optic probe.

49. The apparatus of claim 41, wherein said energy detecting means comprises InGaAs detectors.

50. The apparatus of claim 41, wherein said digitizing means is a 16-bit A/D converter.

51. The apparatus of claim 41, wherein said optical interface is positioned at optimally determined distances from said target measurement site.

52. The apparatus of claim 51, wherein said distances are specified according to layer of the skin tissue to be sampled.

53. The apparatus of claim 52, wherein said optimal distance is approximately 0–300 μm for the upper dermis.

54. The apparatus of claim 52, wherein said optimal distance is approximately 0.3–3 mm for the lower dermis.

55. The apparatus of claim 51, wherein a point of illumination is set through any of a focusing lens and a fiber-optic probe.

56. The apparatus of claim 51, wherein a point of detection is set through any of a starring optical detector or a fiber-optic probe.

57. The apparatus of claim 41 wherein said means for analysis comprises a digital processor programmed to perform an age estimation procedure;

wherein said digital value is passed to said relative age estimation procedure and whereby a relative age estimation is performed.

58. In an apparatus for non-invasively estimating the relative age of a subject, an optical interface comprising:

means for transmitting NIR energy towards a target measurement site on a subject; and means for collecting NIR energy reflected from said measurement site;

wherein said optical interface is adapted to be positioned at optimally determined distances from said site.

59. The optical interface of claim 58, wherein said transmission means is a light pipe, a fiber-optic probe, a lens system, or a light-detecting mirror.

60. The optical interface of claim 58, wherein said energy collecting means comprises at least one starring optical detector.

61. The optical interface of claim 58, wherein said energy collecting means comprises at least one fiber-optic probe.

62. The optical interface of claim 58, wherein said optimal distances are specified according to layer of the skin tissue to be sampled.

63. The optical interface of claim 62, wherein said optimal distance is approximately 0–300 μm fore the upper dermis.

64. The optical interface of claim 62, wherein said optimal distance is approximately 0.3 mm–3 mm for the lower dermis.

65. The optical interface of claim 58, wherein a point of Illumination is set through any of a focusing lens and a fiber-optic probe.

66. The optical interface of claim 58, wherein a point of detection is set through any of a starring optical detector and a fiber-optic probe.

* * * * *